United States Patent
Ellis et al.

(10) Patent No.: US 10,453,669 B2
(45) Date of Patent: Oct. 22, 2019

(54) ELECTRODELESS GAS DISCHARGE LAMPS AND METHODS OF MAKING THE SAME

(71) Applicant: RGF ENVIRONMENTAL GROUP, INC., Riviera Beach, FL (US)

(72) Inventors: Walter B. Ellis, Jupiter, FL (US); Jeffrey David Behary, West Palm Beach, FL (US)

(73) Assignee: RGF ENVIRONMENTAL GROUP, INC., Riviera Beach, FL (US)

( * ) Notice: Subject to any disclaimer, the term of this patent is extended or adjusted under 35 U.S.C. 154(b) by 112 days.

(21) Appl. No.: 15/706,452

(22) Filed: Sep. 15, 2017

(65) Prior Publication Data

US 2018/0082830 A1   Mar. 22, 2018

Related U.S. Application Data

(60) Provisional application No. 62/395,879, filed on Sep. 16, 2016.

(51) Int. Cl.

| H01J 11/00 | (2012.01) |
|---|---|
| H01J 65/04 | (2006.01) |
| H01J 61/36 | (2006.01) |
| H01J 9/24 | (2006.01) |
| H01J 61/34 | (2006.01) |
| A61L 2/08 | (2006.01) |

(52) U.S. Cl.
CPC ............ *H01J 65/042* (2013.01); *H01J 9/247* (2013.01); *H01J 61/34* (2013.01); *H01J 61/361* (2013.01); *H01J 65/048* (2013.01); *A61L 2/088* (2013.01)

(58) Field of Classification Search
None
See application file for complete search history.

(56) References Cited

U.S. PATENT DOCUMENTS

| 3,778,662 A * | 12/1973 | Johnson | H01J 61/34 |
| | | | 313/486 |
| 5,959,405 A * | 9/1999 | Soules | H01J 65/048 |
| | | | 313/113 |
| 8,314,538 B2 * | 11/2012 | Hombach | H01J 9/247 |
| | | | 313/238 |

* cited by examiner

*Primary Examiner* — Vip Patel
(74) *Attorney, Agent, or Firm* — Rothwell, Figg, Ernst & Manbeck, P.C.

(57) ABSTRACT

In some embodiments, an electrodeless lamp may be provided. The lamp may include an outer tube and an inner tube. The inner tube may be sealed to the outer tube to define a sealed space in which a gas may be contained. The gas may be configured to emit electromagnetic radiation when an electromagnetic field is applied thereto.

16 Claims, 8 Drawing Sheets

ELECTRODELESS GAS DISCHARGE LAMPS AND METHODS OF MAKING THE SAME

PRIORITY CLAIM AND CROSS-REFERENCE TO RELATED APPLICATIONS

The present application claims priority to U.S. Provisional Patent Application Ser. No. 62/395,879, filed Sep. 16, 2016, which is hereby incorporated by reference in its entirety.

TECHNICAL FIELD

The present disclosure relates generally to gas discharge lamps and methods of making the same. More particularly, the disclosure relates to electrodeless lamps, which may be constructed with or without phosphors to be used for general lighting purposes or of special glasses to transmit portions of the ultraviolet spectrum as used in water sterilization, air purification, advanced oxidation processes, and kindred applications.

Systems for lighting a lamp are disclosed, including various methods for employing high frequency electronic ballasts or radio frequencies to ensure a long life and high efficiency while requiring minimal maintenance, a minimum amount of safety requirements, and having a minimal effect on the environment in their overall production and disposal.

BACKGROUND

Gas discharge lighting may involve a glass vessel containing low pressure gas and a plurality of electrodes used to ignite the gas. The electrodes supply electrons for the discharge and may be of the cold- or hot-cathode variety. In cold-cathode lamps the gas is ignited by ion bombardment, and in the hot-cathode variety the gas is lit by thermionic emission. In the case of general lighting, the gas discharge contains both portions of visible light and ultraviolet radiation—the spectral output of both depending mainly on the mixes of gases used, the pressure of the gas, the addition of mercury, amalgams, metals, alloys, elements, or combinations thereof. The addition of these components to the lamp also may affect the ease with which the lamps are operated and the steadiness and consistency of the output desired from the lamp.

Phosphors may be added to the inner walls of the lamp to further modify the output of the lamps by increasing the efficiency of visible light portions of the spectrums emitted. Typically, these phosphors are used to convert portions of the ultraviolet spectrums emitted by the mixtures into visible light to make them more efficient or pleasing for general lighting purposes. Black-lights, ultraviolet lamps, germicidal lamps, and spectrum lamps are all gas discharge lamps made of special glasses used to transmit or block portions of the UV and/or visible spectrum for optical or scientific purposes, air or water purification, the curing of glue and adhesives, reaction of chemical processes, germicidal use, the production of catalysts through advanced oxidation processes, and other kindred applications.

The lifespan of gas discharge bulbs may be limited by several factors. One limiting factor is a decreased efficiency of the lamps over time. Typically, this gradual inefficiency is due to a blackening of the inner walls of the glass tubes known in the art as "solarization." In the construction of cold-cathode tubes it is caused by a gradual "sputtering" of the electrodes in starting and in operation where small portions of the metal electrodes are deposited on the glass walls as impurities over time, thus limiting the output. In the construction of hot-cathode lamps tungsten filaments contained on either end of the lamps become incandescent and portions of the metal filaments are boiled off during the thermionic emission process in the starting the lamps. The introduction of tungsten filaments also can also cause lamps to fail prematurely due to mechanical stresses or breakage as in the case of standard incandescent bulbs. In both styles of lamps, the operating voltage, frequency, and current must be critically matched for each lamp to avoid early lamp failures. In both styles of bulbs, there is also a chance of premature failure due to the leakage of the glass-to-metal seals used to secure the metal electrodes into the glass walls of the tube.

In the case of lamps constructed for general lighting, this blackening obscures the ultraviolet portion of the spectrum from reaching the phosphors and causes a reduced output of visual light and efficiency of the lamps over time. In the case of lamps used for the production of ultraviolet radiation, this blackening may also cause chemical reactions with the quartz and/or other glass used in the construction of these lamps, which may also cause a decrease in the ultraviolet production of the lamp. In both types of lamps, this gradual inefficiency may exist and increase even with no apparent detection in the normal starting and operation of the lamps. This may cause lamps to remain in service for periods of time where their usefulness has been reduced to the point of inefficiency.

A further disadvantage of conventional gas discharge lamps is the inability to properly dim the lamps in situations where reduced outputs are desired. Attempts to operate the lamps by varying the voltage or current often results in the lamps simply failing to light altogether, providing very little or no range as to how they are operated.

SUMMARY

Accordingly, there is a need for lamps that feature improved lifespan and efficiency, but which do not suffer from costly and specialized construction requirements.

In some embodiments, an electrodeless lamp may include an outer tube, and an inner tube disposed within the outer tube, the inner tube being hermetically sealed to the outer tube to define a sealed space therebetween. In some embodiments, the space may contain a gas that is configured to emit electromagnetic radiation when an electromagnetic field is applied thereto.

In some embodiments, a method for producing an electrodeless lamp may be provided. The method may include such steps as providing an outer tube, inserting an inner tube within a hollow interior of the outer tube, and providing a gas in a space between the inner and outer tubes. The gas may be configured to emit electromagnetic radiation when an electromagnetic field is applied thereto. In some embodiments, the inner and outer tubes may be hermetically sealed together, thereby defining a seal space in which the gas may be contained.

In some embodiments, an electrodeless lamp may include two open-ended domed tubes. In some embodiments, the tubes may be flared and fused hermetically near their open end and forming a space therebetween. In some embodiments, the space may contain a gas discharge section that can be excited a plurality of ways internally and externally by high frequency electrical fields.

In some embodiments, an electrodeless lamp may include an outer tube and an inner tube, the inner tube being flared outward at both ends to be hermetically sealed to the outer tube. In some embodiments, a space may be formed between the inner and outer tubes. In some embodiments, the space may contain a gas discharge section that can be excited a plurality of ways internally and externally by high frequency electrical fields.

In some embodiments, an electrodeless lamp may include a hollow jacketed body and a gas discharge section. The jacketed body may be open-ended on at least one side. An outer tube of the jacketed body may have an internal coating of a phosphor, UV transmitting glass, UV blocking glass, chemical treatment or other material for modifying the output of the lamp, increase the production of light, transmit or block parts of the UV or visual spectrum, or inhibit chemical reactions on jacketed body.

In some embodiments, an electrodeless lamp may include a jacketed body having a hollow portion therein and a gas discharge section. In some embodiments, the jacketed body may be open-ended on at least one side. In some embodiments, capacitive conductors, induction coils, or any combination thereof may be inserted into the hollow portion without the use of wires hermetically sealed into the glass.

In some embodiments, an electrodeless lamp may include a jacketed body having a hollow portion therein and containing a gas discharge section. In some embodiments, capacitive conductors, induction coils, or any combination thereof may be inserted into the hollow portion to energize the lamp internally without the use of wires hermetically sealed into the glass, and at least one externally grounded conductor may be placed to increase the efficiency of the lamp and facilitate easy starting and the steady operation thereof.

In some embodiments, an electrodeless lamp may include externally grounded conductors that act as catalysts. The catalysts may increase the efficiency of the lamp and facilitate easy starting and the steady operation thereof, and may provide in combination with the normal outputs of the lamp additional compounds as part of secondary reactions resulting from catalytic processes between the spectral output of the lamp and the materials by which the grounded catalyst conductors are constructed.

In some embodiments, an electrodeless lamp may include a hollow jacketed body containing a gas discharge section. The lamp may be excited externally by radio frequency coils. Electrical conductors may be placed inside the hollow of the lamp to intensify the effects.

In some embodiments, an electrodeless lamp may include a hollow jacketed body containing a gas discharge section, the length of which can be much greater than electrodeless lamps produced hitherto because of internally capacitive coupled conductors whose lengths can extend to fill the greater portion of the hollow of the lamp.

In some embodiments, an electrodeless lamp may include a hollow jacketed body containing a gas discharge section. The body may be open-ended on both sides, whereby into the hollow portion of the lamp water, fluids, oils, gases, or air may be passed or circulated for purposes of modification, sterilization, or otherwise enhancement or alternation from the spectral output of the lamp. Conductive coatings can be used to energize the lamp externally and the addition of internal capacities may be added. For example, such features may be used in instances where the mediums to be treated are not sufficiently conductive to act as an electrical ground to intensify the discharge of the lamp.

In some embodiments, an electrodeless lamp may include a hollow jacketed body containing a gas discharge section that may be open-ended on one side or both. In some embodiments, the intensity of light or radiation emitted by the lamp can be varied to a wide extent without fear of extinguishing the discharge by changing the voltage potential of induction coils or capacities with respect to the grounded portions of the lamp.

In some embodiments, an electrodeless lamp may include a hollow jacketed body containing a gas discharge section. The body may be open-ended on one side or both. The lamp may be excited by potential differences of a high frequency electrical field, intensified by grounding or uniting portions of the lamp not coupled directly to the high frequency supply.

In some embodiments, an electrodeless lamp may include a hollow jacketed body containing a gas discharge section. The body may be open-ended on one side or both. In some embodiments, the jacketed wall may form a capillary section of glass tubing containing a gas at low pressure which is easily excitable by high frequency fields. The capillary tubing may produce a discharge of greater intensity than from a tube of the same diameter constructed by ordinary methods.

In some embodiments, an electrodeless lamp may include a hollow jacketed body containing a gas discharge section, open-ended on one side or both, whereby the jacketed wall forms a capillary section of glass tubing containing a gas at low pressure, containing metallic electrodes or silvered or metallized glass located on the surfaces of the interior void and external to the hollow jacketed body which comprises materials which act additionally as visible light or ultraviolet reflectors to increase the output of light or radiation radially along the axis of the lamp 360° and also act as electrical conductors which may be used to energize the lamp or provide an RF ground.

In some embodiments, an electrodeless mercury-free lamp comprising a hollow jacketed body containing a gas discharge section, open-ended on one side or both, whereby the jacketed wall forms a capillary section of glass tubing containing a rare gas or mix of rare gases at low pressure such as xenon or krypton, where internal electrodes and external catalysts are used to energize the lamp and have the discharge take place as a uniform luminous glow as compared to a rope or linear discharge often associated with plasma discharges of these gases at low pressures.

In some embodiments, an electrodeless lamp consisting of a hollow jacketed body containing a gas discharge section, open-ended on one side or both, whereby into the hollow portion of the lamp capacitive conductors which also act as outward projecting reflectors for visible light and/or ultraviolet radiation may be inserted to energize the lamp internally without the use of wires hermetically sealed into the glass, and externally grounded conductors may be placed to increase the efficiency of the lamp and facilitate easy starting and the steady operation thereof.

One object is to provide electrodeless lamps with a construction which is inexpensive, efficient, which has long-life, and is easily produced for a variety of applications.

Another object is to provide a low pressure gas discharge lamp for general lighting purposes or the production of ultraviolet radiation using an electrodeless design and offering a high efficiency, a near indefinite life, and a mechanical structure lending itself to a variety of applications hitherto not possible or practical with electrodeless lamps.

A further object is to provide a lamp having a gas discharge portion that is formed in a closed-loop electrical circuit with an external linear appearance. This may be achieved by using a hollow lamp design with an evacuated jacketed wall, the wall forming the electrical equivalent of a single turn of wire short-circuited in a closed loop.

Particular embodiments of the present invention are directed to electrodeless gas discharge lamps and methods of making the same.

According to one exemplary embodiment, an electrodeless lamp providing a gas discharge for the purpose of illumination, spectral emissions, or producing ultraviolet radiations, comprises: an outer tube; an inner tube disposed within the outer tube, the inner and outer tubes defining a space therebetween; wherein said space contains a gas, said gas being configured to emit electromagnetic radiation when an electromagnetic field is applied thereto.

According to another exemplary embodiment, a method for producing an electrodeless lamp comprises: providing an outer tube; inserting an inner tube within a hollow interior of the outer tube; providing a gas in a space between the inner and outer tubes, said gas being configured to emit electromagnetic radiation when an electromagnetic field is applied thereto; and hermetically sealing the inner and outer tubes together, thereby defining a sealed space that contains the gas.

In another exemplary embodiment, an electrodeless gas discharge lamp and method of making the same may utilize gases for generation of UV light that do not include mercury. Such gases may include, for example, Xenon. Accordingly, construction and operation of the lamps may be environmentally friendly.

BRIEF DESCRIPTION OF THE DRAWINGS

The accompanying drawings, which are incorporated herein and form part of the specification, illustrate various embodiments.

DETAILED DESCRIPTION

Figures 1A, 1B, 1C:
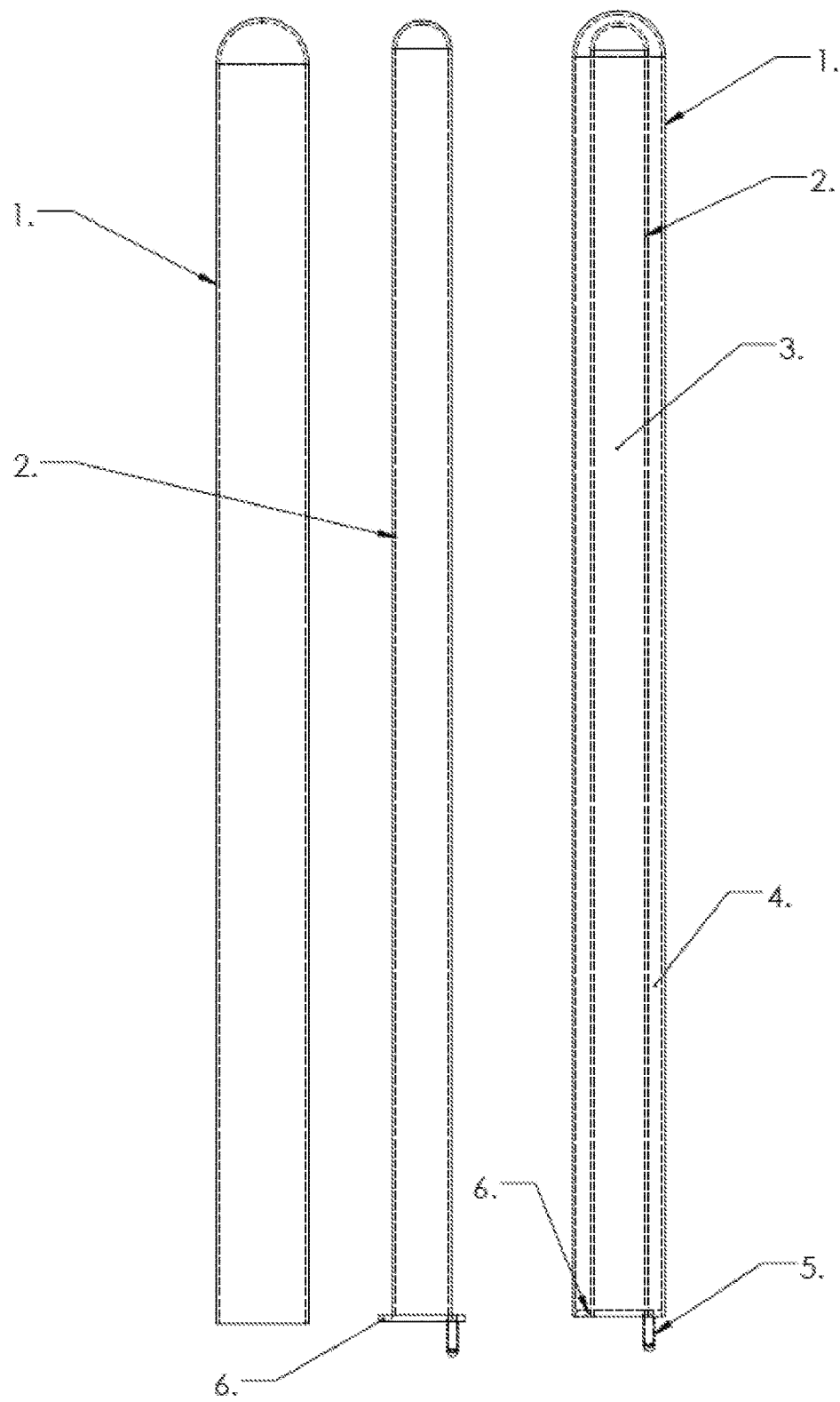
FIG. 1A, FIG. 1B, and FIG. 1C illustrate different views of an open-ended domed glass envelope for a lamp in accordance with exemplary embodiments of the present the invention.

FIG. 1A, FIG. 1B, and FIG. 1C illustrate an exemplary embodiment of a lamp envelope. The lamp may be made of glass, borosilicate, uviol, quartz, fused quartz, ceramics, or any other material suitable for the production of fluorescent, neon, ultraviolet, or gas discharge lamps. The material may be selected to transmit or block the visible or invisible portions of the electromagnetic spectrum the lamp is designed to produce or filter.

The lamp envelope may include an outer tube 1 and an inner tube 2. The inner and outer tubes may be formed in any suitable shape or arrangement. For example, the inner and/or outer tubes may have circular, oval, polygonal, or other cross-sectional shape, and may be straight or curved in a lengthwise dimension. As one example, the inner and/or outer tubes may be substantially cylindrical. The inner and outer tubes 1, 2 may be fused together to form a jacketed body defining a hollow ring. The inner tube 2 may be flared at one end 6 to be easily fused to the outer tube 1. A void 3 may be provided in the inner section of the inner tube 2, and the void 3 may be open to the normal atmosphere. As discussed below with reference to FIGS. 4-6, the void 3 may contain electrical elements used to couple the lamp to a driving circuit for operating the lamp.

A space 4 may be provided between the inner and outer tubes 1, 2. The space 4 may contain a gas at low pressure which may be ionized to produce visible light and/or ultraviolet radiation. The distance between the outermost wall of the inner tube 2 and the innermost wall of the outer tube 1 may be optimized to improve the efficiency and brightness of the lamp by providing a compact discharge path with a high lumens/watt ratio as compared to lamps of large diameter and conventional linear configuration.

A sealing tube 5 may be used in the manufacturing process to evacuate the lamp of air, backfill the lamp with inert gas, and/or insert additives such as mercury, amalgam, metals, or elemental salts for producing a desired spectrum of light or radiations. The sealing tip 5 may be located anywhere on the lamp and in any orientation relative to the longitudinal axis of the lamp. The sealing tip 5 provides a mechanical means for inserting and sealing off the lamp envelope during the manufacturing process with the necessary gas and or gas-mixes required for the lamp to operate efficiently. Any suitable gas may be used. In some aspects, the lamp envelope, which may define a capillary section of glass tubing, may be free from mercury. Likewise, the lamp envelope may contain a rare gas or mix of rare gases at low pressure such as xenon or krypton.

The evacuated space 4 may represent a closed loop of gas and when operated with high or radio frequencies can act as a short-circuited turn of an RF transformer providing a low voltage high current path for the discharge to take place. The void 3 need not extend between the domes of both tubes. In alternative embodiments, lamps may be made with two concentric hollow tubes flared and hermetically sealed at both ends. Other construction methods are suitable as will be understood by those of skill in the art, and do not depart from the scope of the present invention.

Figure 2A:
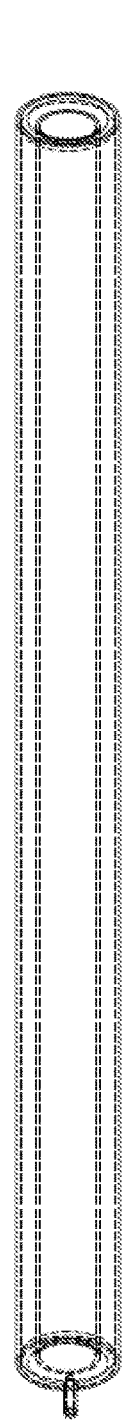
FIG. 2A, FIG. 2B, and FIG. 2C illustrate different views of a double open-ended jacketed cylindrical envelope for a lamp in accordance with exemplary embodiments of the present the invention.
Figure 2B:
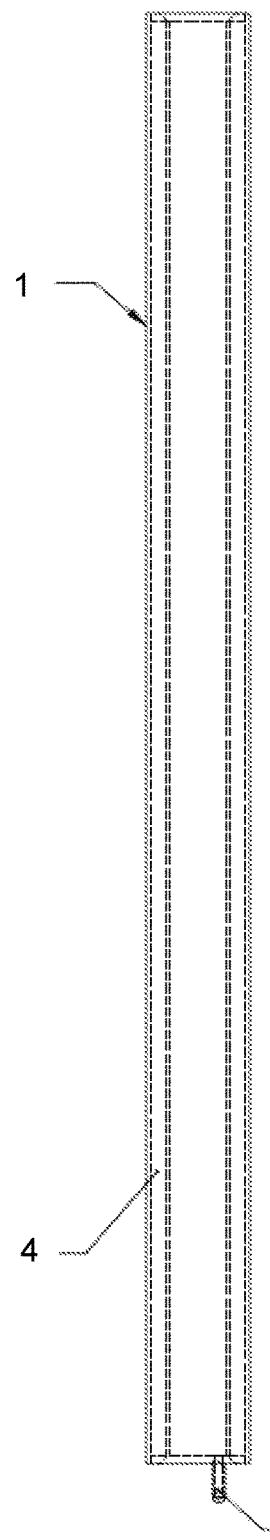
Figure 2C:
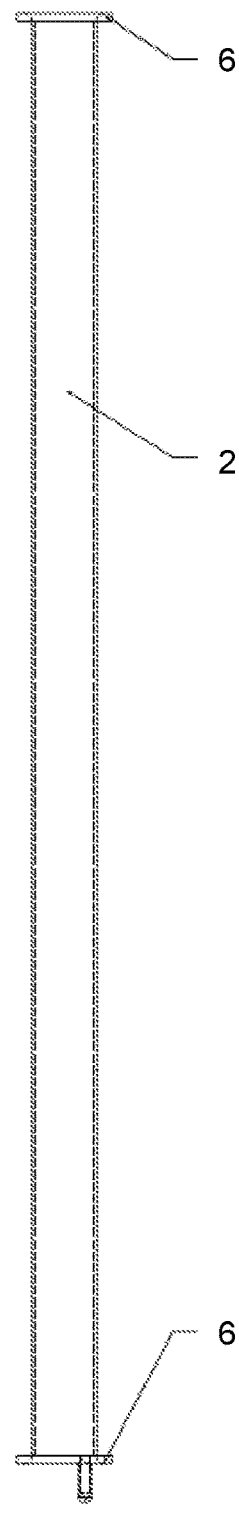

FIG. 2A, FIG. 2B, and FIG. 2C illustrate an exemplary embodiment of a lamp envelope where the lamp body includes two open-ended tubes. An inner tube 2 may be flared at both ends 6. The flared ends 6 may allow the inner tube 2 to be hermetically sealed inside a larger outer glass tube 1. A space 4 may be provided between the outer wall of the inner tube 2 and the inner wall of the outer tube 1, and the space 4 may be arranged to house low pressure gas for vacuum discharge.

Figures 3A, 3B:
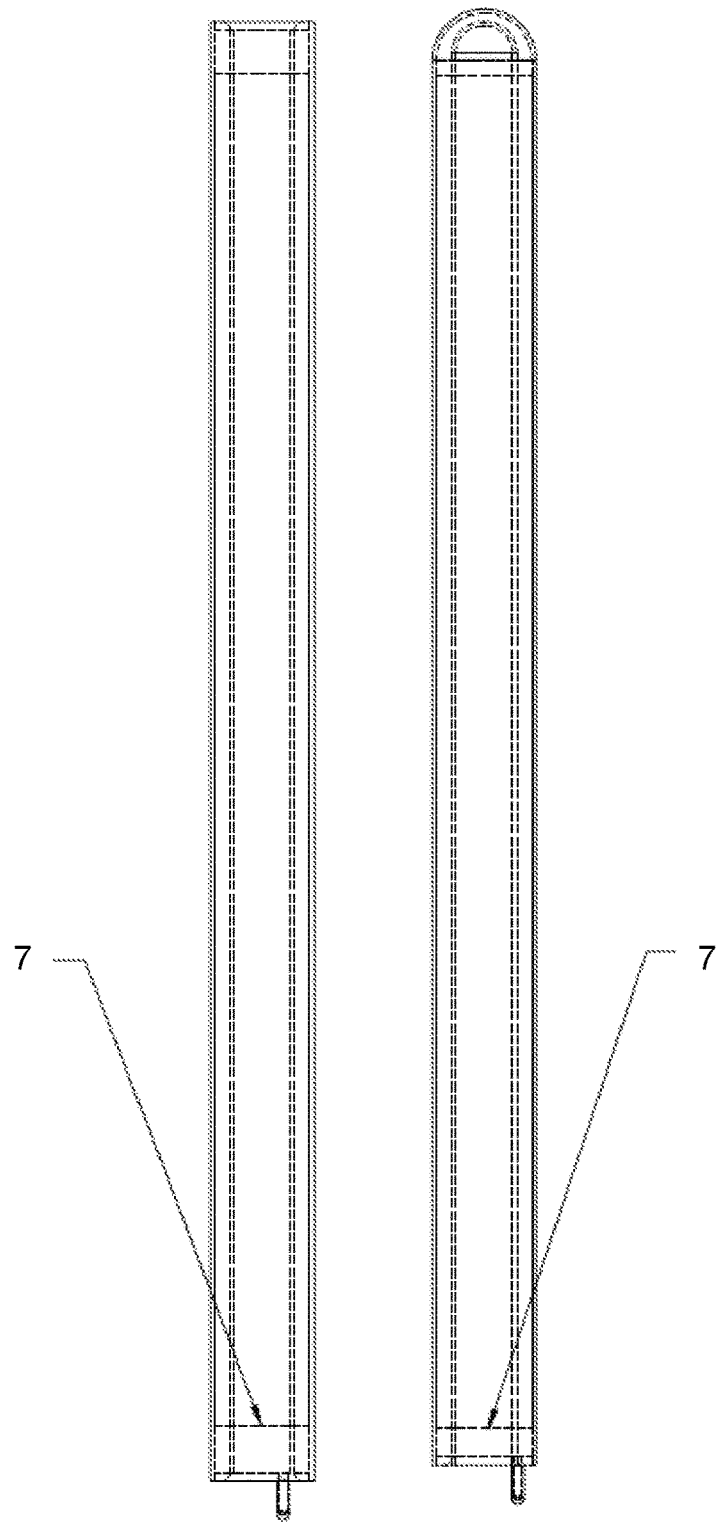
FIG. 3A and FIG. 3B illustrate different views of a double open-ended or open-ended domed envelope for a lamp, containing a phosphor for the production of fluorescent light, or a coating to limit, modify, or provide extended life in the production of ultraviolet radiation in accordance with exemplary embodiments of the present the invention.

FIG. 3A and FIG. 3B depict an exemplary embodiment where a phosphor 7 is provided in or on the lamp envelope. In some aspects, the phosphor may be provided as a coating disposed on the inner or outer surface of the outer tube. The phosphor may be specific in the production of fluorescent light or reduction, alteration, or enhancement of ultraviolet radiation as may be the case. The phosphor may include any material known in the art to produce or modify the output of the light or radiation. It can be made of rare earth elements, halo-phosphate type phosphors, or any element used primarily to convert ultraviolet radiation to light, or to block portions of ultraviolet spectrum (e.g., cerium, Wood's glass, etc.) from being transmitted as in the case of black-light or standard ultraviolet lamps, germicidal lamps, lamps producing spectral outputs useful for producing catalytic reactions, etc. Similarly a coating may be applied to prevent chemical reactions in the lamp, protect the glass walls from mercury contamination, or otherwise add to the longevity or quality of light or radiation intended to be produced. In the case of black-lights, fluorescent lamps, ultraviolet lamps, and otherwise a lamp with a jacketed vessel allows the reduction of the cost of the lamp by using phosphor-coated or otherwise expensive glasses only in the portion of the lamp needed to produce the desired effects (whether light or radiation). The inner and outer tubes may be made from the same material, or alternatively, different materials may be used. Thus, two different materials may be used in situations where doing so may be more cost-effective or convenient.

Figures 4A, 4B:
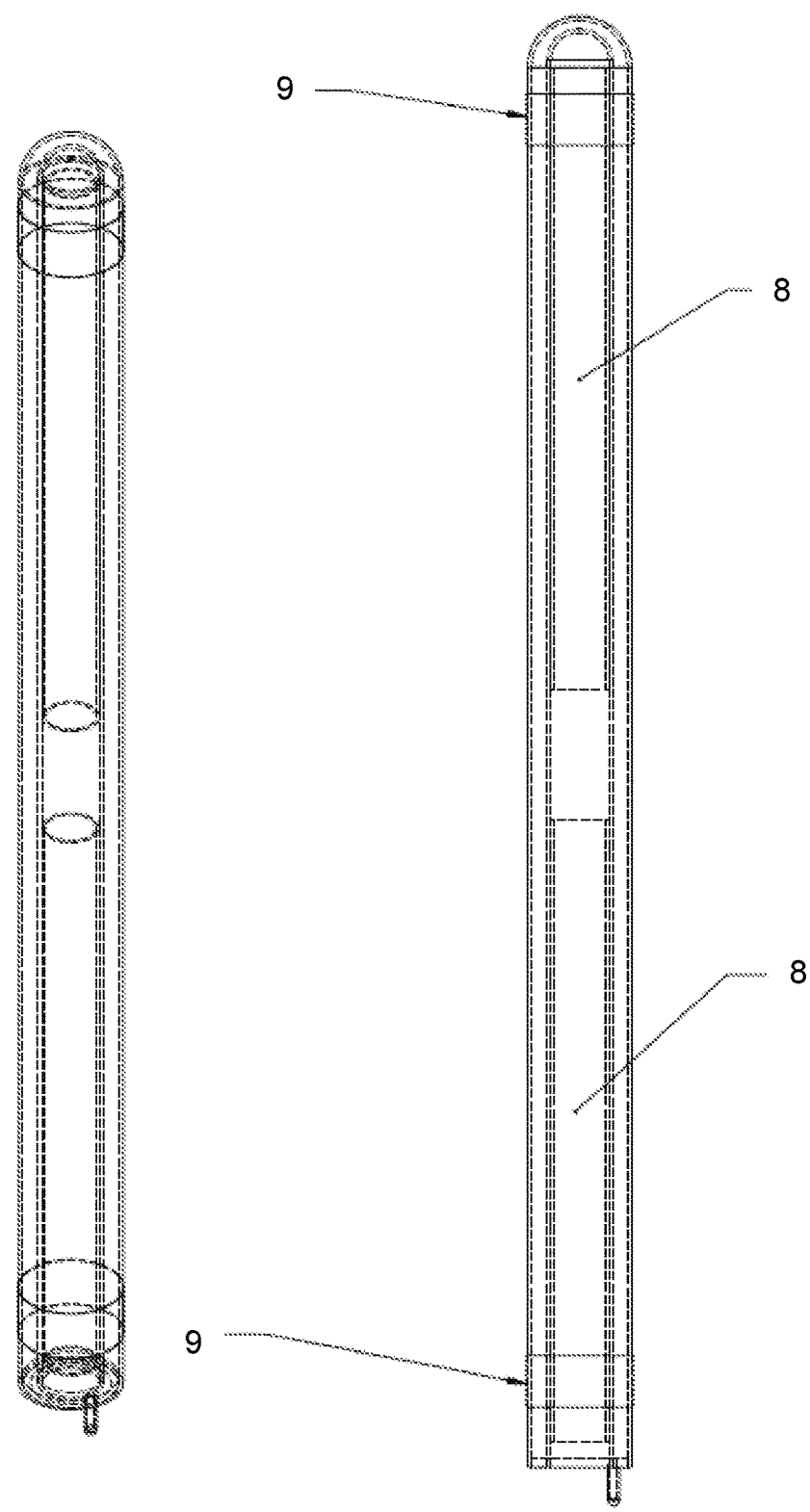
FIG. 4A and FIG. 4B illustrate different views of lamp with internal and external foil coatings to be operated by capacitive coupling using radio frequency currents in accordance with exemplary embodiments of the present the invention.

FIG. 4A and FIG. 4B illustrate an exemplary embodiment in which conductive elements 8, 9 are provided on the inner and/or outer surfaces of the lamp in order to allow the ignition of the lamp gas with radio frequency or oscillatory currents. In some aspects, an applied current or electrical field may travel in at least partially radial direction between the inner and outer conductive elements 8, 9. The conductive elements may be foil, metallic, or otherwise conductive coatings. The conductive elements 8, 9 may be disposed externally to the vacuum portion of the lamp, thus preventing contaminations from forming inside of the vacuum during operation. The void within the inner tube may contain inner conductive elements 8, which may be for example easily insertable foil coatings. The outer conductive elements 9 may be made smaller and can be electrically grounded to each other conveniently by spring clips, brackets, or other mechanical connections which can be used simultaneously to mount the lamp inside of a fixture. If the voltage of the oscillatory circuit is high enough, only one foil or coating may be used. Similarly, the higher frequency currents used to drive and ballast the lamp can reduce the size of outer conductive elements 9 or even eliminate them entirely if operated in the Megahertz or Gigahertz range, as with short wave radio frequencies or microwave energy. In some embodiments, a low cost lamp can be operated at frequencies ranging from 20 kHz to 250 kHz. In these embodiments, it may be beneficial to provide both internal and external conductive elements. The length of the inner conductive elements 9 may be varied according to the needs of a given application, and in some embodiments, may extend along the full length of the inner void. By using longer conductive elements, the cross-sectional area of the conductive path may be extended, which may thereby provide increased current flow at relatively lower voltages. This may be particularly advantageous when using gases such as xenon or krypton, for which application of high voltages may be associated with undesirable roping or linear discharge effects.

The inner conductive elements 8 may be provided with live electrical connections where they are shielded from users. The outer conductive elements 9 may be an electrical ground to complete the RF circuit and enhance the field and intensity of the discharge between the outer jacketed sections of the lamp. In other embodiments, the lamp may be operated with live electrical connections externally and grounded conductive elements internally. The location, size and scope of the conductive elements may be varied without departing from the scope of the invention. Similarly, the conductive elements can be made of metal foil, conductive tape, conductive paint or adhesive, metals deposited onto the glass, metallic screens, meshes, solid metal rods, or any other form of electrical connection or conductor which can be inserted in to the cavity and in some embodiments may be removed from the lamp for service or inspection. The operating frequency of the lamp is not critical to the scope of the invention, which envisions operation in the kilohertz, megahertz, gigahertz range and beyond.

Figures 5A, 5B, 5C:
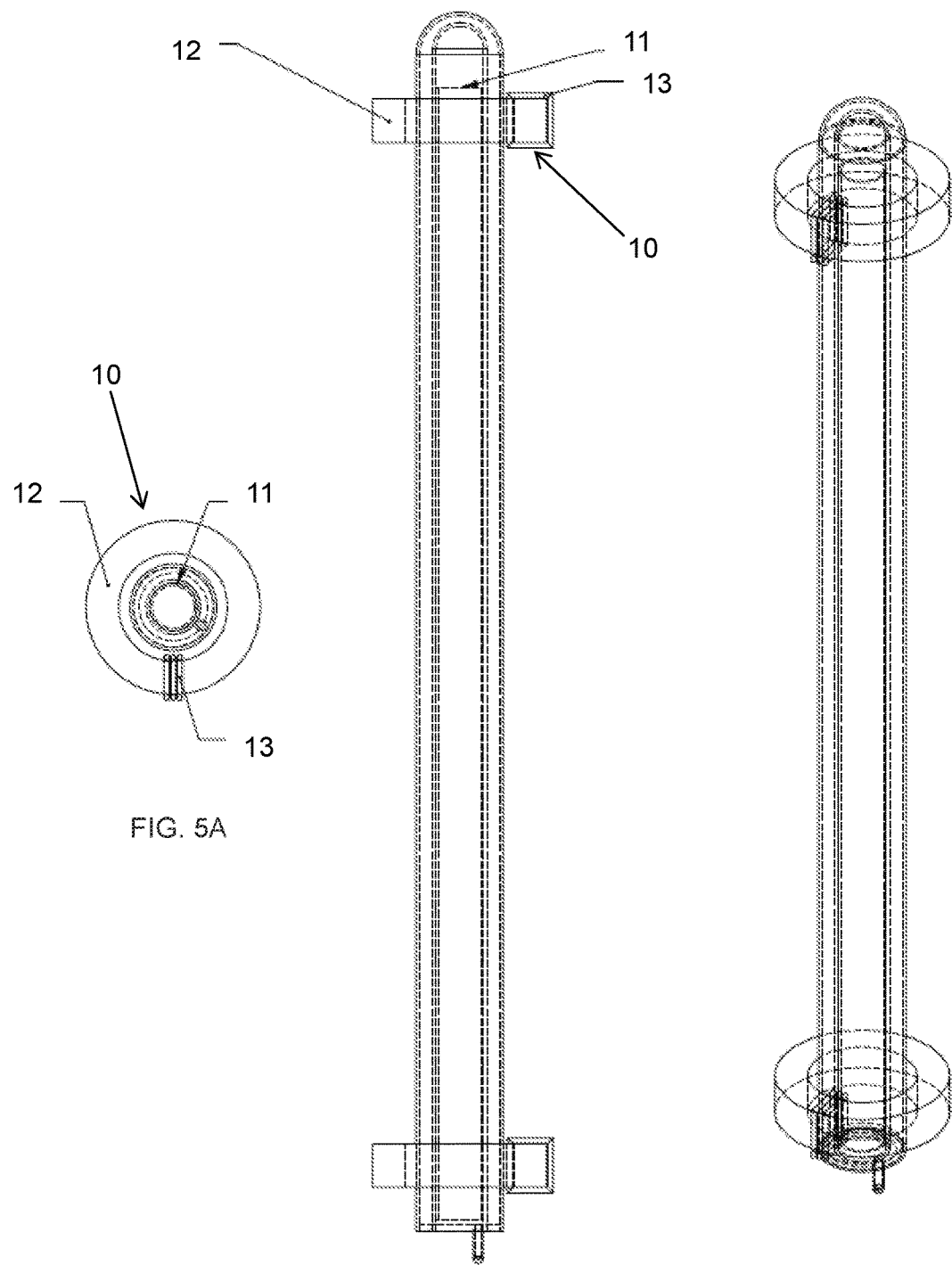
FIG. 5A, FIG. 5B, and FIG. 5C illustrate different views of a lamp with external radio frequency coils to operate the lamp by methods of induction in accordance with exemplary embodiments of the present the invention.

FIG. 5A, FIG. 5B, and FIG. 5C illustrate an exemplary embodiment in which external coils 13 are used to light the lamp by induction. The inner section of the lamp may contain a foil or otherwise conductive coating 11 to facilitate starting and steady operation of the lamp. Radio frequency (RF) chokes 10 may be provided and may function as inductors 10. Each inductor 10 may function as the primary winding of a transformer while the gas inside the jacketed envelope of the lamp may function as a one-turn secondary coil, falling within the high frequency field and inducing lower voltage and higher currents through the gas discharge section of the lamp by induction. The inductor 10 may include a ferrite core 12 wrapped with a layer of insulated wire 13 into which high frequency currents are energized. The inductor 13 shown here has three turns of wire for convenience but may contain any number of turns required to excite the gas with the proper level of luminosity and intensity based on the ballast used. The number of inductors may be varied to suit the needs of a given application. For example, a shorter lamp may be operated using only one inductor if the glass envelope of the lamp is not too long. Depending on the length of the lamp and electrical requirements of its operation, the lamp may be lit externally by one, two, or a plurality of inductors. As discussed above, energizing the gas via elements disposed along the length of the lamp may allow for higher current at relatively lower voltages. This may be particularly advantageous when using gases such as xenon or krypton, for which application of high voltages may be associated with undesirable roping or linear discharge effects.

Figures 6A, 6B:
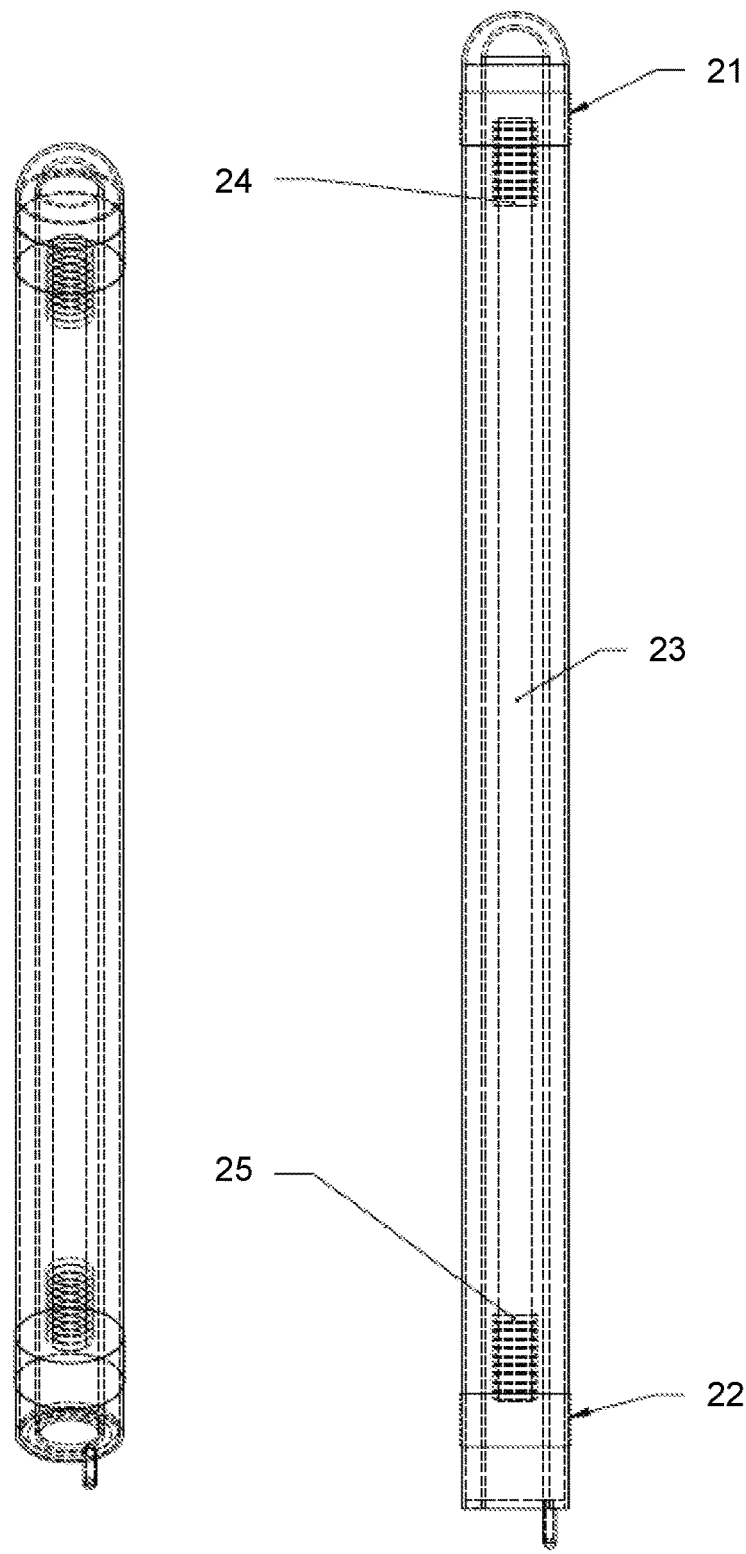
FIG. 6A and FIG. 6B illustrate different views of a lamp with internal radio frequency coils to operate the lamp by methods of induction in accordance with exemplary embodiments of the present the invention.

FIG. 6A and FIG. 6B illustrate an exemplary embodiment in which internal coils 24, 25 are used to light the lamp by induction. The outer section of the lamp may contain a foil or otherwise conductive coatings 24 and 25 which may be grounded and electrically united to facilitate starting and steady operation of the lamp. The RF chokes may function as inductors and may act as the primary winding of a transformer while the gas inside the jacketed envelope of the lamp acts like a one-turn secondary coil, falling within the high frequency field and inducing lower voltage and higher currents through the gas discharge section of the lamp by induction. The inductors are composed of a ferrite rod 23 wrapped with layers of insulated wire 24 and 25 into which high frequency currents are energized. The coils 24 and 25 shown here have ten turns of wire for convenience but may contain any number of turns required to excite the gas with the proper level of luminosity and intensity based on the ballast used. The number of coils provided may be varied to suit the needs of a given application. Moreover, when providing AC power, the oscillatory phases of the inductors may be varied, and in some aspects, may be opposite from one coil to the next. A relatively shorter lamp may be operated using only one inductor. In other embodiments, the lamp may be lit internally by one, two, or a plurality of coils as determined by the length of the lamp and electrical requirements of the operating the same.

Figure 7:
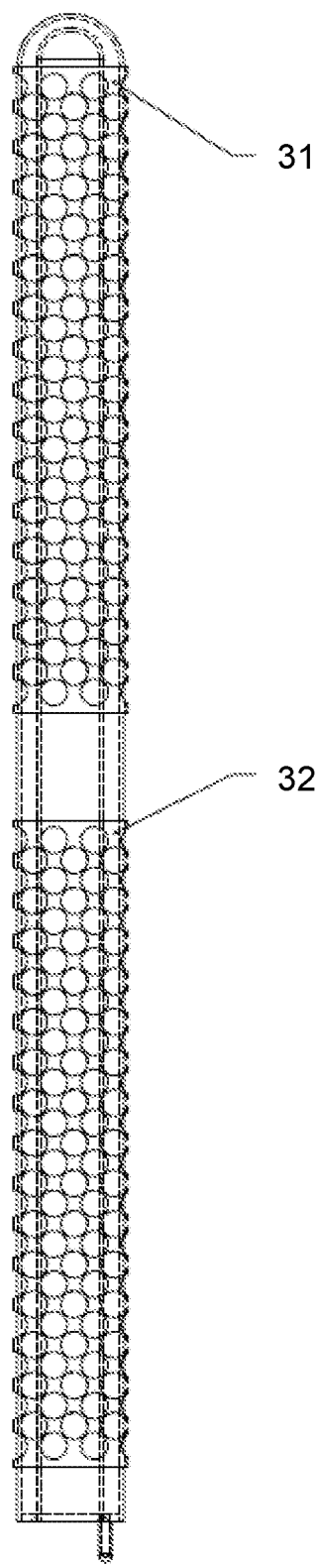
FIG. 7 illustrates an exemplary embodiment of a lamp with external conductive sleeves that can act additionally as catalysts for creating advanced oxidation products when used for generating ultraviolet radiation in accordance with exemplary embodiments of the present the invention.

FIG. 7 illustrates an exemplary embodiment in which dual purpose external electrically conductive catalysts 31, 32 are coupled to the lamp body for the production of advanced oxidation products when used for ultraviolet light or sterilization processes. The lamp may be powered through the open central cavity by either capacitive coupling as outlined in FIG. 4 or by induction internally using methods outlined in FIG. 6. Catalysts 31 and 32 may be metallic sleeves or mesh which can be treated or painted with Titanium Dioxide, powdered metals, reactive chemicals, or any combination of items known in the art to promote catalytic processes in combination with ultraviolet radiation, light, germicidal wavelengths, allotropes of oxygen, or any combination thereof produced by the lamps in normal operation. In addition these catalysts may be composed of materials electrically conductive (such as aluminum) and serve a dual purpose of grounding the outside sections of the lamp and providing a more concentrated electrical field around the jacketed portion of the lamp to allow easier starting and facilitate the steadiness and consistency in the operation of the lamp. The more concentrated field also produces a higher concentrated output of light, ultraviolet radiation, or any combination thereof at the external surface of the tube nearest the catalyst. The catalyst conductor may be provided according to any suitable construction, including the use of perforated materials, mesh, screen, solid conductors, close-coupled reflectors, split tubing, or otherwise electrically conductive structures which can contain a catalyst and serve a dual purpose of intensifying the electrical field around the lamp body.

By using an outer conductive member that permits light to pass therethrough, the conductive member may extend for a substantial length along the exterior of the lamp, or in some embodiments, may extend along the full length of the lamp. By extending the conductive elements along a greater portion of the length of the lamp, the cross-sectional area of the conductive path may be extended, which may thereby provide increased current flow at relatively lower voltages. This may be particularly advantageous when using gases such as xenon or krypton, for which application of high voltages may be associated with undesirable roping or linear discharge effects.

Figures 8A, 8B:
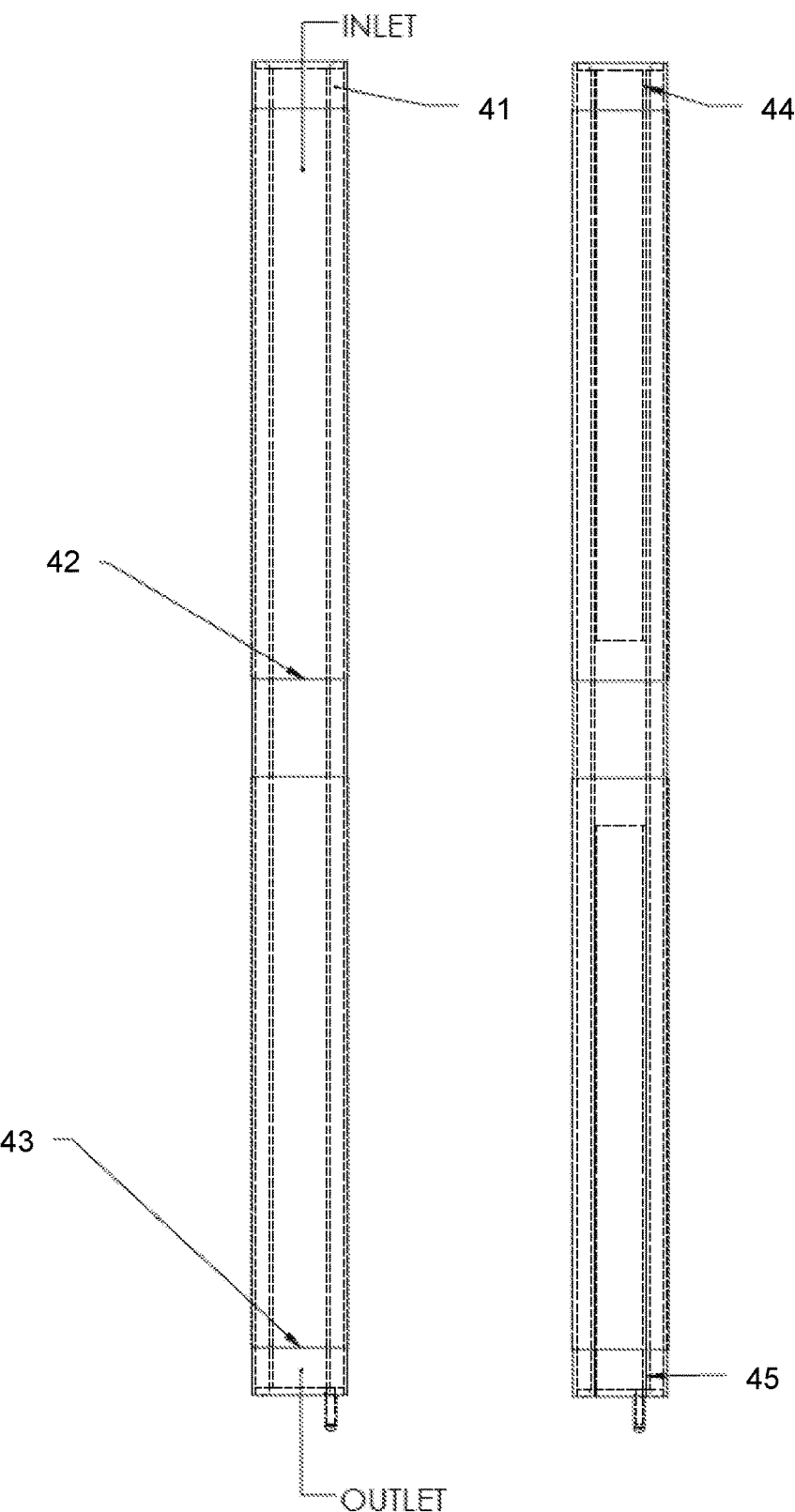
FIG. 8A and FIG. 8B illustrate different of a lamp with external conductive coatings, open-ended on both ends, in which waters, fluids, oils, gases, or airs may be passed through the hollow of the lamp to be treated, modified, sterilized, or otherwise affected by the spectral output of the lamp while in operation in accordance with exemplary embodiments of the present the invention.

FIG. 8A and FIG. 8B illustrate an exemplary embodiment in which the lamp is open on both ends 41 and dual metallic conductors 42 and 43 are placed outside of the lamp for means of excitation. Water, fluids, oils, gases, or airs may be passed through the open ends of the tube 41. In this manner, a passing medium may be sterilized, modified, treated, or otherwise affected by the spectral outputs of the lamp in a closed-loop system. Either of the open ends 41 may be the inlet or outlet for the medium flow to be treated. The medium flow may be coupled to the lamp body ends by any means known in the art for the medium intended to be treated. In instances where the medium to be treated is conductive or semi-conductive, capacitive coupling of internal electrodes is not needed as the internal medium will act as a ground to intensify the output of the lamp. For mediums with insulating properties, grounded conductive tubes 44 and 45 such as hollow aluminum or stainless steel can be inserted into the void of the lamp to intensify the discharge.

As set forth above, an improved form of electrodeless gas discharge lamp which is operated easily and efficiently by standard frequencies used in electronic ballasts and with a linear design lending itself to any standard application of typical gas discharge lamps is disclosed. While preferred embodiments of the invention are disclosed it is possible to energize the lamp a variety of ways combining techniques herein. Moreover, other variations will be apparent to those of skill in the art and will not deviate from the scope of the present invention.

For example, a lamp might be lit using high frequency and a combination of both coils and capacitances. The lamp may also be made to operate wirelessly using Tesla Coils, radio frequencies, short wave frequencies, microwave radiation, etc. Such embodiments may be accomplished by varying capacity and inductance or any combination thereof to act as antennas, transmitters, conductors, or otherwise termed methods of transferring energy at those frequencies well-known by those skilled in the art.

Disclosed above are electrodeless lamps, which may be devoid of internal electrodes, and may prevent the general blackening of the bulbs over time and greatly increase their useful life. Among other benefits, the arrangements described above permit cost-effective construction, ballasting, and sealing.

While various embodiments of the present disclosure are described herein, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the processes described above and illustrated in the drawings are shown as a sequence of steps, this was done solely for the sake of illustration. Accordingly, it is contemplated that some steps may be added, some steps may be omitted, the order of the steps may be re-arranged, and some steps may be performed in parallel.

The invention claimed is:

1. A lamp comprising:
   an outer tube comprising a first cylindrical body;
   an inner tube comprising a second cylindrical body, the inner tube being disposed within the outer tube;
   an annular seal extending radially between an end of the inner tube and an end of the outer tube, the outer tube, inner tube, and annular seal collectively defining a sealed space between the outer tube and inner tube, the sealed space containing a gas configured to emit electromagnetic radiation when an electromagnetic field is applied thereto; and
   a sealing tube extending from the annular seal, the sealing tube being configured for use in evacuating the lamp of air.

2. The lamp of claim 1, further comprising a first electrical conductor, wherein an inner surface of the inner tube defines a void, the first electrical conductor being at least partially disposed within the void.

3. The lamp of claim 2, wherein the void is open to the atmosphere at an end of the lamp.

4. The lamp of claim 2, further comprising a second electrical conductor, the second electrical conductor being disposed outwardly relative to an outer surface of the outer tube such that the sealed space is positioned between the first and second electrical conductors.

5. The lamp of claim 1, wherein a phosphor is provided on a surface of at least one of the outer tube and the inner tube.

6. The lamp of claim 1, further comprising an inductor, the inductor being arranged to apply energy for exciting the gas in the sealed space.

7. The lamp of claim 1, further comprising an electrically conductive catalyst layer, the catalyst layer being configured to (i) apply energy for exciting the gas in the sealed space, and (ii) facilitate the production of advanced oxidation products.

8. A method for producing a lamp, the method comprising the steps of:
providing an outer tube comprising a first cylindrical body;
inserting an inner tube within a hollow interior of the outer tube, the inner tube comprising a second cylindrical body;
sealing the inner tube to the outer tube using an annular seal extending radially between an end of the inner tube and an end of the outer tube, the outer tube, inner tube, and annular seal collectively defining a sealed space between the inner tube and the outer tube; and
inserting, using a sealing tube extending from the annular seal, a gas into the sealed space between the inner and outer tubes, said gas being configured to emit electromagnetic radiation when an electromagnetic field is applied thereto.

9. A method of using a lamp comprising:
providing a lamp comprising:
an outer tube comprising a first cylindrical body;
an inner tube disposed within the outer tube, the inner tube comprising a second cylindrical body;
an annular seal extending radially between an end of the inner tube and an end of the outer tube, the outer tube, inner tube, and annular seal collectively defining a sealed space between the inner tube and the outer tube; and
a first electrical element, the electrical element being selected from the group consisting of an electrical conductor and an inductor;
wherein the space contains a gas, the gas being configured to emit electromagnetic radiation when an electromagnetic field is applied thereto; and
applying energy to the gas contained within the sealed space using the electrical element, wherein applying the energy results in the gas emitting light.

10. The method of claim 9, wherein an inner surface of the inner tube defines a void, and the first electrical element is at least partially disposed within the void.

11. The method of claim 10, wherein the void is open to the atmosphere at an end of the lamp.

12. The method of claim 10, wherein the lamp further comprises a second electrical element, the second electrical element being disposed outwardly relative to an outer surface of the outer tube such that the sealed space is positioned between the first and second electrical conductors.

13. The method of claim 12, wherein the energy is a radio frequency excitatory signal applied between the first electrical element and the second electrical element.

14. The method of claim 9, wherein a phosphor is provided on a surface of at least one of the outer tube and the inner tube.

15. The method of claim 9, wherein the electrical element is an inductor, the inductor being arranged to apply energy for exciting the gas in the sealed space.

16. The method of claim 9, wherein the electrical element comprises an electrically conductive catalyst layer, the catalyst layer being configured to (i) apply the energy to the gas in the sealed space, and (ii) facilitate the production of advanced oxidation products.

* * * * *